United States Patent [19]

Hayes et al.

[11] Patent Number: 5,721,123
[45] Date of Patent: Feb. 24, 1998

[54] METHODS AND APPARATUS FOR DIRECT HEATING OF BIOLOGICAL MATERIAL

[75] Inventors: Donald J. Hayes, Plano; David B. Wallace, Dallas; Christopher J. Frederickson, Little Elm, all of Tex.

[73] Assignee: MicroFab Technology, Inc., Plano, Tex.

[21] Appl. No.: 583,425

[22] Filed: Jan. 5, 1996

[51] Int. Cl.$^6$ .................................................. C12P 19/34
[52] U.S. Cl. ........................... 435/91.1; 435/6; 435/7.1; 435/91.2; 436/501
[58] Field of Search .................. 250/504 R, 454.11, 250/455.11, 493.1; 422/52, 62, 68.1, 82.08, 82.09, 82.12, 109; 435/290, 291, 91.1, 6, 7.1, 91.2; 935/78, 79, 87, 88; 436/501

[56] References Cited

U.S. PATENT DOCUMENTS

| | | | |
|---|---|---|---|
| 5,229,297 | 7/1993 | Schnipelsky et al. | 436/94 |
| 5,302,347 | 4/1994 | Van Den Berg et al. | 422/67 |
| 5,411,876 | 5/1995 | Bloch et al. | 435/91.2 |
| 5,415,839 | 5/1995 | Zaun et al. | 422/64 |
| 5,498,392 | 3/1996 | Wilding et al. | 422/68.1 |
| 5,503,721 | 4/1996 | Hearst et al. | 204/157.6 |
| 5,508,197 | 4/1996 | Hansen et al. | 435/285.1 |
| 5,538,848 | 7/1996 | Livak et al. | 435/5 |
| 5,565,339 | 10/1996 | Bloch et al. | 435/91.2 |

*Primary Examiner*—Charles T. Jordan
*Assistant Examiner*—John R. Hardee
*Attorney, Agent, or Firm*—Locke Purnell Rain Harrell

[57] ABSTRACT

Biological material is cycled through a sequence of temperatures by containing the material in a vessel positioned in a chamber maintained at a temperature which is no higher than the lowest temperature in a predetermined temperature sequence. The vessel is then irradiated with varying levels of electromagnetic radiation to heat the material and cycle it through a sequence of predetermined temperatures.

12 Claims, 1 Drawing Sheet

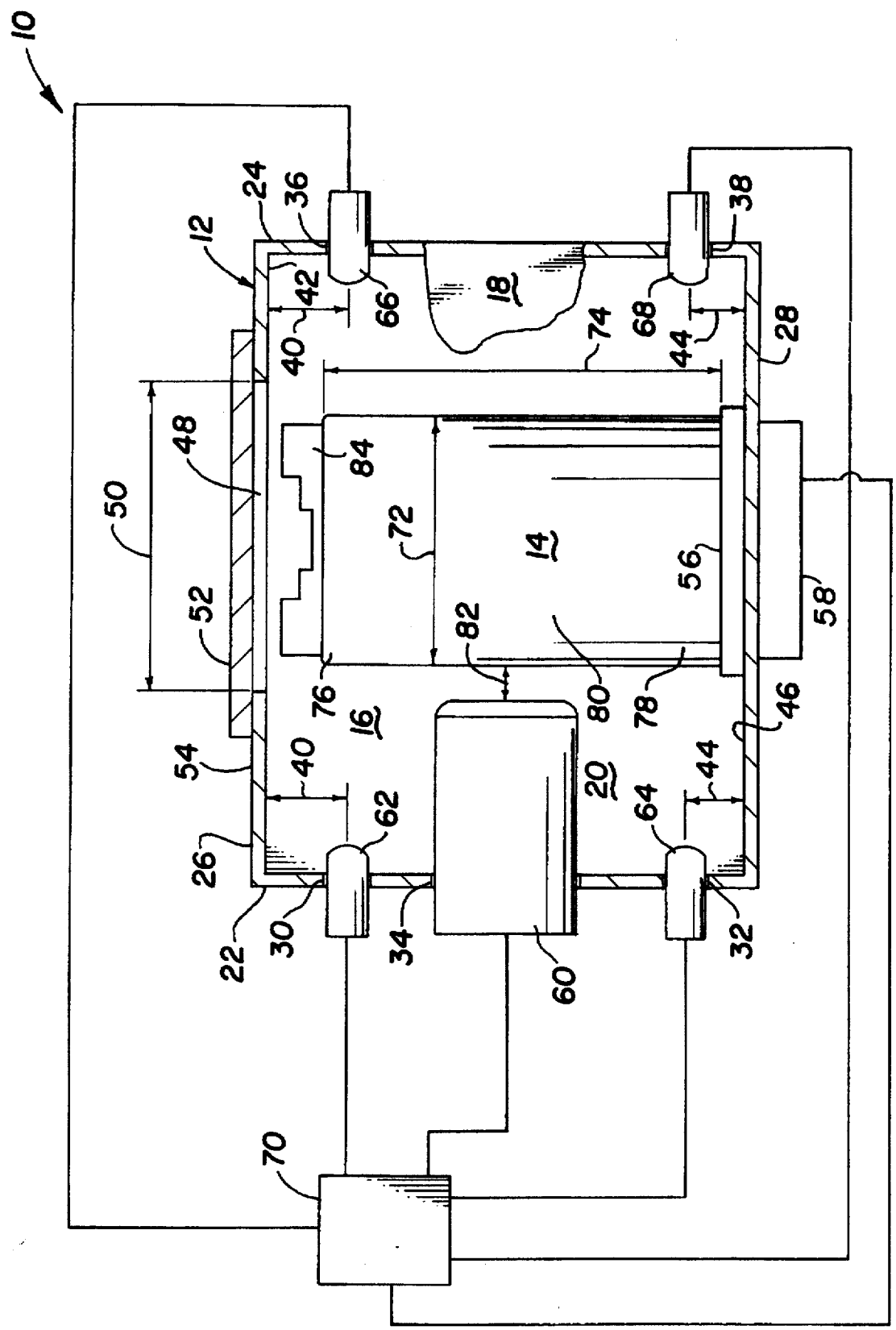

METHODS AND APPARATUS FOR DIRECT HEATING OF BIOLOGICAL MATERIAL

This invention relates to cycling biological material through predetermined temperature sequences. More particularly, it relates to methods and apparatus for changing the temperature of material in a vessel by exposing the vessel to electromagnetic radiation.

Genetic testing of DNA and related materials is an integral part of clinical, commercial and experimental biology. In the medical field, for example, genetic tests are critical for effective treatment of cancer and inherited diseases. Oncologists use genetic tests to obtain the cytogenetic signature of a malignancy which in turn guides the choice of therapy and improves the accuracy of prognoses. Similarly, monitoring the frequency and type of mutations persisting after chemotherapy or radiation therapy provides a quick and accurate assessment of the impact of the therapy. Perhaps the most important application of molecular diagnosis in oncology is the emerging possibility of using anti-sense genetic therapy to combat tumor growth.

Inherited diseases occur when a person inherits one or two copies of a defective version (referred to hereinafter as an allele) of a gene. Genetic tests can be used to determine which genes and alleles thereof are responsible for a given disease. Once the gene is identified, further testing can identify carriers of the allele and aid researchers in designing treatments for the disease.

Most genetic tests begin by amplifying a portion of the DNA molecule from a sample of biological material. Amplification is made practical by the polymerase chain reaction (PCR) wherein a DNA synthesizing enzyme (polymerase) is used to make multiple copies of a targeted segment of DNA. By repeating the polymerase copying process, many copies of the targeted segment are produced. For example, thirty (30) repetitions can produce over one million (1,000,000) copies from a single molecule.

Changing the temperature (thermo-cycling) of the test sample drives the PCR reaction. The optimum thermo-cycle varies depending on the material amplified and the result sought. In typical PCR processes the sample is heated and cooled to three (3) different target temperatures and maintained at each target temperature for a length of time sufficient for the sample to undergo a desired change.

Thermo-cycling typically begins with heating the sample to about 95° C. to separate the double strands and make them accessible as templates for polymerase replication. Cooling to about 55° C. allows the polymerase initiators (primers) to hybridize with their target DNA segments. Control of temperature during the hybridization process is critical for accurate hybridization of the primer to the DNA. Different primers have different optimal hybridization temperatures. Heating from 55° C. to about 72° C. is necessary for efficient performance of the polymerase enzyme. At the appropriate temperature, the polymerase reaction catalyzes the elongation of new DNA complementary in nucleotide sequence to the target DNA. At the end of the elongation reaction, heating the solution to 95° C. causes the newly formed double-stranded DNA to separate into single strands, thus providing templates for another round of PCR amplification.

Current thermo-cycling methods are complex, time consuming and expensive. One thermo-cycling device (known as the MJ Research DNA engine) comprises a surface upon which are placed micro-wells and under which rests a thermoelectric block for heating and cooling biological material placed in the wells. However, this device takes about one and one-half (1.5) minutes to perform each cycle, even when using a simplified two temperature format. The device thus requires approximately forty-five (45) minutes to perform a thirty cycle run.

Various devices using capillary tubes can perform a thirty cycle run in from ten to thirty minutes. These devices require loading and unloading samples to and from the tubes, sealing the tubes and then exposing the tubes to forced air heating. When the loading and unloading steps are included, these procedures may consume as much as two hours of laboratory time.

One conventional thermo-cycler uses forced water circulation to heat and cool vessels immersed in a water bath. Three or more reservoirs hold water at different temperatures and rapid pumps and valves bring water from the reservoirs into the bath to produce a large thermal mass which heats or cools the material in the vessels. Another device used in PCR processes (See European Patent No. 381501) utilizes a flexible bag-like structure with an inner system of chambers. The DNA sample and reagent fluids are loaded into the chambers and the bag is placed on a hot plate for thermo-cycling. After thermo-cycling, the bag is squeezed with external rollers to move the fluid into chambers containing detection reagents.

Using conventional methods and apparatus a significant amount of the thermo-cycle time is occupied by ramp periods wherein the temperature of the material is changed from one target temperature to the next. The length of the ramp period is a function of thermo-cycling method and volume of material amplified. Current methods and apparatus must heat the test chamber first. The test chamber then transfers heat to the material contained therein. The sizes of typical test chambers and the volumes of material contained therein result in thermal inertia and poor surface area to volume ratios.

Current methods and apparatus typically pose further time limitations by generating only one thermo-cycle at a time. Thus, to process multiple PCR samples at their optimum thermo-cycles requires processing the samples one after the other (serial processing). Serial processing may be avoided by using multiple thermo-cyclers, but this approach consumes capital, energy and laboratory space.

Parallel processing can be used to process multiple DNA samples simultaneously. The most common parallel processing technique involves grouping several DNA samples together and subjecting them to a common thermo-cycle. However, the common cycle is necessarily a compromise among optimum cycles and time savings are thus achieved at the expense of quality of results.

BRIEF DESCRIPTION OF THE DRAWING

FIG. 1 is a somewhat schematic configuration of the invention illustrating the apparatus and a control system for operating the apparatus.

In accordance with the present invention electromagnetic radiation is used as an energy source for heating. A source of electromagnetic radiation is positioned to irradiate the vessel containing the material sample. The vessel is equipped with conventional fittings for automatic loading of unprocessed biological material and is surrounded by a chamber which is maintained at a temperature at least as low as the lowest temperature in the desired temperature sequence.

A fluid sample of the biological material is placed in the vessel and subjected to electromagnetic radiation to heat the material to a desired first target temperature. To change the temperature of the material to the next target temperature in the sequence, the level of irradiation is either increased or decreased. If the lowest temperature in the sequence is sought, the level of irradiation is reduced to zero and the temperature of the material allowed to equalize with that of the chamber. For faster cooling, active pull-down may be accomplished by holding the chamber at a temperature well below the target temperature.

If desired, the fluid placed in the vessel may include fluorescent labels for analyzing the amplified product, thermochromic dyes for monitoring the temperature of the fluid, and/or heat absorptive dyes (including thermochromic dyes) for enhancing the heating effect of the electromagnetic radiation. The apparatus may employ visible and/or ultraviolet light sources and optical sensors for monitoring the temperature of the fluid and/or analyzing the amplified product.

Direct heating significantly reduces the time required to perform the PCR process. Since electromagnetic radiation directly heats the fluid sample, the steps of heating a hot plate, heating a water bath, etc., and heating the vessel walls are eliminated. The need to heat the center core of the solution via convective heating from the outer surfaces is also obviated. Furthermore, by directly exciting molecules in the solution, the thermal lag and lead delays (ramp periods) normally associated with conventional methods can be substantially reduced or eliminated. Moreover, by using thermochromic dyes the reaction solution temperature may be monitored with optical sensing to minimize temperature overshoot and undershoot. By using thermochromic dye as the absorber, the temperature can be automatically "clamped" at the phase-change temperature of the dye. Various other features and advantages of the invention will become more readily understood from the following detailed description taken in connection with the appended claims and attached drawing which is a partially schematic and partially sectional view of apparatus employing the preferred embodiment of the invention.

Direct heating apparatus embodying a preferred form of the invention is designated generally by the reference numeral 10 in the drawing. Apparatus comprises a housing 12, vessel 14 and a variety of components described in detail hereinafter which control the temperature of a fluid sample placed in the vessel 14 and analyze the results of the reaction which takes place in the vessel.

Housing 12 forms a chamber 16 defined by a front wall 18, rear wall 20, left side wall 22, right side wall 24, top wall 26 and bottom wall 28. The walls may be integrally formed to provide a unitary housing structure as shown or one or more walls can be separately formed and secured to the other walls using conventional materials and techniques.

Light source holes 30 and 32 extend through the left side wall 22. Left side wall 22 also includes an electromagnetic radiation source hole 34 positioned between the top wall 26 and bottom wall 28. Optical sensor holes 36 and 38 extend through the right side wall 24. Light source hole 30 and optical sensor hole 36 are positioned in alignment with each other a distance 40 from the interior surface 42 of top wall 26. Light source hole 32 and optical sensor hole 38 are also positioned in alignment with each other a distance 44 above the interior surface 46 of bottom wall 28.

An entrance hole 48 having a diameter 50 is located in top wall 26 approximately midway between the left and right side walls 22 and 24. Lid 52 is positioned on the top wall exterior surface 54 to cover entrance hole 48. The lid 52 can be opened to provide access to the chamber 16 through the entrance hole 48. Interior surface 46 of bottom wall 28 includes a mounting fixture 56 positioned in alignment with entrance hole 48.

A thermoelectric device 58 is secured to and in thermal contact with the chamber 16. The thermoelectric device is operable to pump heat either out of or into the chamber 16 to maintain the chamber at desired temperatures. Other conventional devices such as hot and/or cold air blowers may be used for the same purpose.

Housing 12 may be provided without a top wall 26 so that the chamber 16 is exposed to the temperature of the environment outside the housing. In any embodiment where the chamber is exposed to the temperature of the environment outside the housing, it is to be understood that such environment makes up all or a portion of the "chamber" as the term is used herein. For example, apparatus can be provided wherein the chamber comprises the laboratory room in which the apparatus is located.

A source 60 of electromagnetic radiation (referred to hereinafter as an "energy source") is positioned in hole 34 and oriented to transmit electromagnetic energy toward the center of the chamber 16. The energy source 60 irradiates the vessel 14 to heat the fluid sample therein. The preferred energy source is a conventional diode array laser (greater than 25 Watts) which produces energy in the visible range of the electromagnetic spectrum. A similar laser which produces energy in the near infrared portion of the electromagnetic spectrum may also be used. Similarly, the energy source may be a gas laser or a conventional microwave source.

First light source 62 is positioned in hole 30 and second light source 64 is positioned in hole 32. Each of the light sources preferably emit energy in either the visible or ultraviolet ranges of the electromagnetic spectrum. A combination of one visible light and one ultraviolet light source may be used if desired. Each light source is oriented to direct energy across the center of the chamber toward the optical sensor holes 36 and 38.

First optical sensor 66 is positioned in hole 36 and second optical sensor 68 is positioned in hole 38. The optical sensors are preferably of the type used for either fluorimetric or absorptiometric analysis and are positioned to receive light emitted by the first and second light sources, respectively, or to receive fluorescent emissions induced by either source 62 or 64. The sensors used may vary depending on the type of light sources 62 and 64 used to provide the sensor input, the material to be analyzed, and thermochromic and other materials placed in the biological sample undergoing the PCR process, etc.

A controller 70 and the connections thereto are represented schematically. The controller may be any device or devices capable of controlling the energy source 60, first and second light sources 62 and 64, first and second optical sensors 66 and 68, and the thermoelectric device 58 to provide the desired thermo-cycle described hereafter.

Vessel 14 is provided for holding the sample biological material and is made from material which transmits the electromagnetic radiation emitted by the electromagnetic energy source 60. The material is also transparent to light emitted by the first and second light sources.

The vessel 14 is installed in the chamber 16 through entrance hole 48 and is removably secured to mounting fixture 56. The height 74 of vessel 14 is less than the distance between interior surface 42 and mounting fixture surface 58, thus permitting the vessel to be positioned upright within the chamber 16. The upper portion 76 of the vessel 14 is positioned between the first light source 62 and the first optical sensor 66. The lower portion 78 of the vessel is positioned between the second light source 62 and the second optical sensor 68. The central portion 80 of the vessel is positioned a distance 82 from the energy source 60 so that all (or at least a major portion of) the electromagnetic energy emitted into the chamber 16 is absorbed by the material in the vessel 14.

The upper portion 76 of the vessel 14 includes a fluid fitting 84 for connecting to automated loading apparatus (not shown). The fluid fitting 84 and entrance hole 48 are sized to permit loading of reagents and biological samples into the vessel 14 by automated or other means after the vessel is positioned on the mounting fixture 56. However, the vessel 14 may be pre-loaded with reagents and/or biological samples prior to insertion into the chamber.

The apparatus described above is readily adaptable to process multiple biological samples simultaneously at the optimum thermo-cycle of each. For example, multiple housings 12 may be connected together at the front and rear walls 18 and 20, respectively. Each housing may support an energy source 60, first and second light sources 62 and 64, first and second optical sensors 66 and 68 and a thermoelectric device 58. Each housing and its supporting apparatus thus forms an independently controllable unit, each of which may provide a different thermo-cycle for processing material contained therein.

In operation, vessel 14 is filled with a fluid sample which may comprise combinations of reagents and other materials necessary to perform the desired reaction, the biological material which undergoes reaction, heat absorptive pigments or dyes (including thermo-chromic pigments or dyes) and/or labeling materials for analyzing the material after the reaction. Examples of heat absorptive pigments which will absorb laser energy in the visible and near infrared portions of the electromagnetic spectrum and which are essentially inert in this application include carbon dust and indocyanine green dye.

Thermochromic dyes may be used to measure temperature of the fluid sample and may also be used in lieu of or in conjunction with the heat absorptive pigments. A suitable thermochromic dye which absorbs laser energy to produce heat is microencapsulated cholesteric crystallin. This material changes its crystalline structure with temperature, causing it to change color. It ceases to absorb energy and change color at specified temperatures, thus may be used to regulate the temperature of the fluid. Another thermochromic dye which could be used for monitoring is temperature sensitive phosphor as currently used in fluorescence decay thermography.

The composition of the fluid sample may vary depending on factors such as type of process to be performed, the biological material to be processed, the type of electromagnetic energy used to heat the sample, and the method used to analyze the sample after the reaction takes place. For example, a fluid sample which will be heated using microwaves will generally not require heat absorptive pigment dispersed therein since microwave energy will heat the water molecules in the fluid sample.

Various portions of the fluid sample may be loaded into the vessel at different times. For example, the vessel 14 can be pre-loaded with the reagents necessary to perform a desired reaction. The laboratory which performs the reaction may add the biological material, heat absorptive pigments, etc. Since the laboratory receives the vessel partially loaded, the number of steps which must be performed by technicians in the laboratory is reduced. As an alternative example, empty vessels may be shipped from the factory to the laboratory.

After the vessel is filled with fluid sample and in place in the housing 12, controller 70 signals the energy source 60, first light source 62 and thermoelectric device 58 to begin operation. The energy source irradiates the vessel 14 to raise the temperature of the fluid sample. Depending on the type of electromagnetic radiation emitted and the composition of the fluid sample, the radiation heats the fluid sample by acting on the heat absorptive pigment, thermochromic dye, water molecules or combinations thereof. The first light source 62 emits light through the fluid sample to the first optical sensor 66 (which monitors the light for variations caused by changes in the optical characteristics of the thermochromic dye). The thermoelectric device maintains the chamber at or below the lowest temperature in the desired temperature sequence.

If the reaction being performed is the PCR reaction hereinbefore described, the fluid sample is heated until it reaches the first target temperature of about 98° C. The thermochromic dye changes color at this temperature and the first optical sensor 66 (which detects variations in the light received from the first light source 62) signals the controller indicating that the first target temperature has been reached. The fluid is maintained at this temperature for the desired time period.

The fluid sample is lowered to the next target temperature of 55° C. by reducing the level of radiation absorbed by the vessel and allowing the heat in the fluid sample to transfer into the chamber. When 55° is reached, the characteristics of the thermochromic dye change and the first optical sensor 66 notifies the controller 70. The response of the controller depends on whether the chamber is to be maintained at or below 55° C. Maintaining the chamber at 55° C. minimizes the possibility of overshooting the target temperature and the fluid sample can be maintained at this temperature without input from energy source 60. Alternatively, maintaining the chamber at a temperature lower than 55° C. requires drawing the temperature of the fluid sample down more rapidly. Once 55° C. is reached, however, irradiation from the energy source may be required to prevent the temperature from dropping even lower.

Since 55° C. (about 99° F.) is above standard room temperature, the temperature of the environment outside the housing 12 (the laboratory temperature, for example) may be used to lower the temperature of the fluid sample. This may be accomplished by providing a housing without a top, side walls, etc., thus exposing the vessel to its surrounding environment.

After the fluid sample has been maintained at 55° C. for a sufficient period of time, the controller 70 signals the energy source to increase the level of irradiation until the next target temperature (about 72° C.) is reached. The thermochromic dye responds at this temperature and the controller 70 is signaled by the first optical sensor 66 to maintain the fluid sample at the required temperature for the desired time period.

The foregoing process may be repeated any number of times. After the thermo-cycle is complete, the controller signals the second light source 62 to illuminate the material in the vessel so that it may be analyzed by the second optical sensor 68.

The direct heating method and apparatus described above substantially reduces the complexity of the PCR procedure. By using radiation to heat the sample, the necessity of making the vessel small or coupling it tightly to hot and/or cold plates is eliminated. Furthermore, the inclusion of appropriate fittings for automatic loading and optical sensors for post-reaction analysis reduces the number and complexity of steps which must be performed by technicians in the laboratory or clinical setting. It will be recognized, therefore, that the principles of the invention may be employed in various arrangements to obtain the benefits of the advantages and features disclosed. Accordingly, it is to be understood that although numerous characteristics and advantages of the invention have been set forth together with details of the structure and function of various embodiments of the invention, this disclosure is illustrative only. Various changes and modifications may be made, especially in matters of shape, size and arrangement of parts, without departing from the spirit and scope of the invention as defined by the appended claims.

What is claimed:

1. A method of cycling biological material through a sequence of temperatures for effecting a bio-chemical reaction, including at least an initial reaction temperature and an elevated reaction temperature above the initial reaction temperature, comprising the steps of:

(a) placing biological material in a vessel;

(b) selecting a thermochromic material which has a phase change at the elevated reaction temperature;

(c) placing the selected thermochromic material in the vessel;

(d) irradiating the contents of the vessel with an amount of electromagnetic radiation sufficient to raise the biological material in the vessel to the elevated reaction temperature; and (e) controlling the temperature of the vessel at the elevated reaction temperature for a reaction time by means of the phase change in the thermochromic material.

2. The method of claim 1 further including the step of sensing the phase change of the thermochromic material at or just above the elevated reaction temperature to indicate the temperature of the biological material.

3. The method of claim 1 wherein the step of selecting the thermochromic material comprises the step of selecting a thermochromic material which has a state between the initial reaction temperature and the elevated reaction temperature which absorbs said electromagnetic radiation and the step of irradiating the contents of the vessel includes the step of raising the temperature of said contents to the elevated reaction temperature by means of absorption of the electromagnetic radiation in the thermochromic material.

4. The method of claim 3 wherein the step of selecting the thermochromic material comprises the step of selecting a thermochromic material which has a state above the phase change at the elevated reaction temperature which does not absorb said electromagnetic radiation whereby the step of controlling the elevated reaction temperature is obtained by clamping caused by repeated phase changes in the thermochromic material.

5. The method of claim 4 further including the step of sensing the phase change of the thermochromic material at or just above the elevated reaction temperature to indicate the temperature of the biological material.

6. A method as set forth in claim 4 including the step of analyzing the results of any reaction involving the biological material as a result of temperature cycling.

7. A method as set forth in claim 6 wherein the step of analyzing the results of the reaction includes labeling the biological material with a fluorescent material, exposing the vessel to a second light source, and measuring the response of the fluorescent material to the second light source.

8. A method as set forth in claim 6 wherein results of the reaction are analyzed using absorptometric analysis.

9. The method of claim 4 wherein the step of irradiating the contents of the vessel is the step of irradiating with laser energy and the steps of selecting and placing a thermochromic material in the vessel are carided out with a thermochromic material which absorbs said laser energy before said phase change at the elevated reaction temperature and does not absorb said laser energy after said phase change at the elevated reaction temperature.

10. A method of cycling biological material through a sequence of temperatures for effecting a bio-chemical reaction, including at least an initial reaction temperature and an elevated reaction temperature above the initial reaction temperature, comprising the steps of:

(a) placing biological material in a vessel transparent to electromagnetic radiation;

(b) selecting a thermochromic material which has a state between the initial reaction temperature and the elevated reaction temperature which absorbs electromagnetic radiation and different state at or just above the elevated reaction temperature which does not absorb said electromagnetic radiation;

(c) placing the selected thermochromic material in the vessel;

(d) irradiating the contents of the vessel with an amount of said electromagnetic radiation more than sufficient to raise the contents in the vessel to the elevated reaction temperature; and (e) clamping the temperature of the contents of the vessel for a reaction time during continued electromagnetic radiation by means of changes of state of the thermochromic material for a reaction time to keep the temperature of the vessel contents close to the elevated reaction temperature.

11. The method of claim 9 further including the step of determining when the contents of the vessel have reached the elevated reaction temperature by sensing the change of state in the thermochromic material.

12. The method of claim 10 wherein the step of irradiating the contents of the vessel is the step of irradiating with laser energy and the steps of selecting and placing a thermochromic material in the vessel are carried out with a thermochromic material which absorbs said laser energy before said phase change at the elevated reaction temperature and does not absorb said laser energy after said phase change at the elevated reaction temperature.

* * * * *